(12) United States Patent
Jaquet et al.

(10) Patent No.: US 10,874,461 B2
(45) Date of Patent: *Dec. 29, 2020

(54) SYSTEMS AND METHODS FOR DETERMINING AND VISUALIZING A FUNCTIONAL RELATIONSHIP BETWEEN A VASCULAR NETWORK AND PERFUSED TISSUE

(71) Applicant: HeartFlow, Inc., Redwood City, CA (US)

(72) Inventors: Clara Jaquet, Paris (FR); Michiel Schaap, Mountain View, CA (US); Ying Bai, Belmont, CA (US); Leo Grady, Millbrae, CA (US); Charles A. Taylor, Menlo Park, CA (US)

(73) Assignee: HeartFlow, Inc., Redwood City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/528,263

(22) Filed: Jul. 31, 2019

(65) Prior Publication Data
US 2019/0350655 A1 Nov. 21, 2019

Related U.S. Application Data

(63) Continuation of application No. 15/088,512, filed on Apr. 1, 2016, now Pat. No. 10,405,925.
(Continued)

(51) Int. Cl.
*G06T 15/00* (2011.01)
*A61B 34/10* (2016.01)
(Continued)

(52) U.S. Cl.
CPC .............. *A61B 34/10* (2016.02); *A61B 34/25* (2016.02); *G06F 3/048* (2013.01); *G16H 50/50* (2018.01); *A61B 2034/105* (2016.02)

(58) Field of Classification Search
CPC ........ G16H 50/50; A61B 34/25; A61B 34/10; A61B 2034/105; G06F 3/048
(Continued)

(56) References Cited

U.S. PATENT DOCUMENTS 8,315,812 B2 11/2012 Taylor
10,307,131 B2 * 6/2019 Taylor .................... A61B 6/032
(Continued)

FOREIGN PATENT DOCUMENTS

JP 2011-516108 A 5/2011
WO WO 2009/109905 A2 9/2009

OTHER PUBLICATIONS

Kim KH, Kang D, Kang N, Kim JY, Lee HE, Kim JD. Patient-specific coronary artery blood flow simulation using myocardial volume partitioning. InMedical Imaging 2013: Computer-Aided Diagnosis Mar. 18, 2013 (vol. 8670, p. 867019). International Society for Optics and Photonics.*
(Continued)

*Primary Examiner* — Phu K Nguyen
(74) *Attorney, Agent, or Firm* — Bookoff McAndrews, PLLC

(57) ABSTRACT

Systems and methods are disclosed for creating an interactive tool for determining and displaying a functional relationship between a vascular network and an associated perfused tissue. One method includes receiving a patient-specific vascular model of a patient's anatomy, including at least one vessel of the patient; receiving a patient-specific tissue model, including a tissue region associated with the at least one vessel of the patient; receiving a selected area of the vascular model or a selected area of the tissue model; and generating a display of a region of the tissue model corresponding to the selected area of the vascular model or a
(Continued)

display of a portion of the vascular model corresponding to the selected area of the tissue model, respectively.

20 Claims, 9 Drawing Sheets

Related U.S. Application Data

(60) Provisional application No. 62/141,895, filed on Apr. 2, 2015.

(51) Int. Cl.
*G16H 50/50* (2018.01)
*A61B 34/00* (2016.01)
*G06F 3/048* (2013.01)

(58) Field of Classification Search
USPC .......................................................... 345/418
See application file for complete search history.

(56) References Cited

U.S. PATENT DOCUMENTS

| 10,405,925 | B2* | 9/2019 | Jaquet | G06F 3/048 |
| 10,497,476 | B2* | 12/2019 | Singer | G06F 30/23 |
| 10,517,678 | B2* | 12/2019 | Taylor | G16H 50/70 |
| 2015/0038860 | A1 | 2/2015 | Fonte et al. | |

OTHER PUBLICATIONS

International Search Report and Written Opinion for corresponding Application No. PCT/US2016/025536 dated Jul. 4, 2016 (12 pages).
Office Action issued in corresponding Japanese Application JP 2017-551074, dated Jan. 17, 2020.

* cited by examiner

SYSTEMS AND METHODS FOR DETERMINING AND VISUALIZING A FUNCTIONAL RELATIONSHIP BETWEEN A VASCULAR NETWORK AND PERFUSED TISSUE

RELATED APPLICATION(S)

This patent application is a continuation of and claims the benefit of priority to U.S. Nonprovisional patent application Ser. No. 15/088,512 filed on Apr. 1, 2016, which claims the benefit of priority to U.S. Provisional Application No. 62/141,895 filed Apr. 2, 2015, the entire disclosures of which are hereby incorporated herein by reference in their entireties.

FIELD OF THE DISCLOSURE

Various embodiments of the present disclosure relate generally to functional assessments of a patient's body, visualizations, and related methods. More specifically, particular embodiments of the present disclosure relate to systems and methods for creating an interactive tool for determining and displaying a functional relationship between a vascular network and an associated perfused tissue.

BACKGROUND

Many forms of disease treatment and assessment exist, including evaluations of various risks to a patient, cost, and treatment efficacy. For example, several solutions exist to prevent and treat coronary heart disease, a leading cause of death worldwide. Assessments of disease severity and/or cause can improve treatment. Disease or disease severity may be linked to issues with blood supply. Insights into vasculature supplying tissue regions may help triage or quickly target an area for further assessment and/or treatment. Thus, a desire exists for assessments that can show functional relationship(s) between a vascular network and a perfused organ.

The foregoing general description and the following detailed description are exemplary and explanatory only and are not restrictive of the disclosure.

SUMMARY

According to certain aspects of the present disclosure, systems and methods are disclosed for creating an interactive tool for determining and displaying a functional relationship between a vascular network and an associated perfused tissue.

One method includes: receiving a patient-specific vascular model of a patient's anatomy, including at least one vessel of the patient; receiving a patient-specific tissue model, including a tissue region associated with the at least one vessel of the patient; receiving a selected area of the vascular model or a selected area of the tissue model; and generating a display of a region of the tissue model corresponding to the selected area of the vascular model or a display of a portion of the vascular model corresponding to the selected area of the tissue model, respectively.

In accordance with another embodiment, a system for creating an interactive tool for determining and displaying a functional relationship between a vascular network and an associated perfused tissue: a data storage device storing instructions for creating an interactive tool for determining and displaying a functional relationship between a vascular network and an associated perfused tissue; and a processor configured for: receiving a patient-specific vascular model of a patient's anatomy, including at least one vessel of the patient; receiving a patient-specific tissue model, including a tissue region associated with the at least one vessel of the patient; receiving a selected area of the vascular model or a selected area of the tissue model; and generating a display of a region of the tissue model corresponding to the selected area of the vascular model or a display of a portion of the vascular model corresponding to the selected area of the tissue model, respectively.

In accordance with another embodiment, a non-transitory computer readable medium for use on a computer system containing computer-executable programming instructions for performing a method of creating an interactive tool for determining and displaying a functional relationship between a vascular network and an associated perfused tissue, the method comprising: receiving a patient-specific vascular model of a patient's anatomy, including at least one vessel of the patient; receiving a patient-specific tissue model, including a tissue region associated with the at least one vessel of the patient; receiving a selected area of the vascular model or a selected area of the tissue model; and generating a display of a region of the tissue model corresponding to the selected area of the vascular model or a display of a portion of the vascular model corresponding to the selected area of the tissue model, respectively.

Additional objects and advantages of the disclosed embodiments will be set forth in part in the description that follows, and in part will be apparent from the description, or may be learned by practice of the disclosed embodiments. The objects and advantages of the disclosed embodiments will be realized and attained by means of the elements and combinations particularly pointed out in the appended claims.

It is to be understood that both the foregoing general description and the following detailed description are exemplary and explanatory only and are not restrictive of the disclosed embodiments, as claimed.

BRIEF DESCRIPTION OF THE DRAWINGS

The accompanying drawings, which are incorporated in and constitute a part of this specification, illustrate various exemplary embodiments, and together with the description, serve to explain the principles of the disclosed embodiments.

DESCRIPTION OF THE EMBODIMENTS

Figure 1:
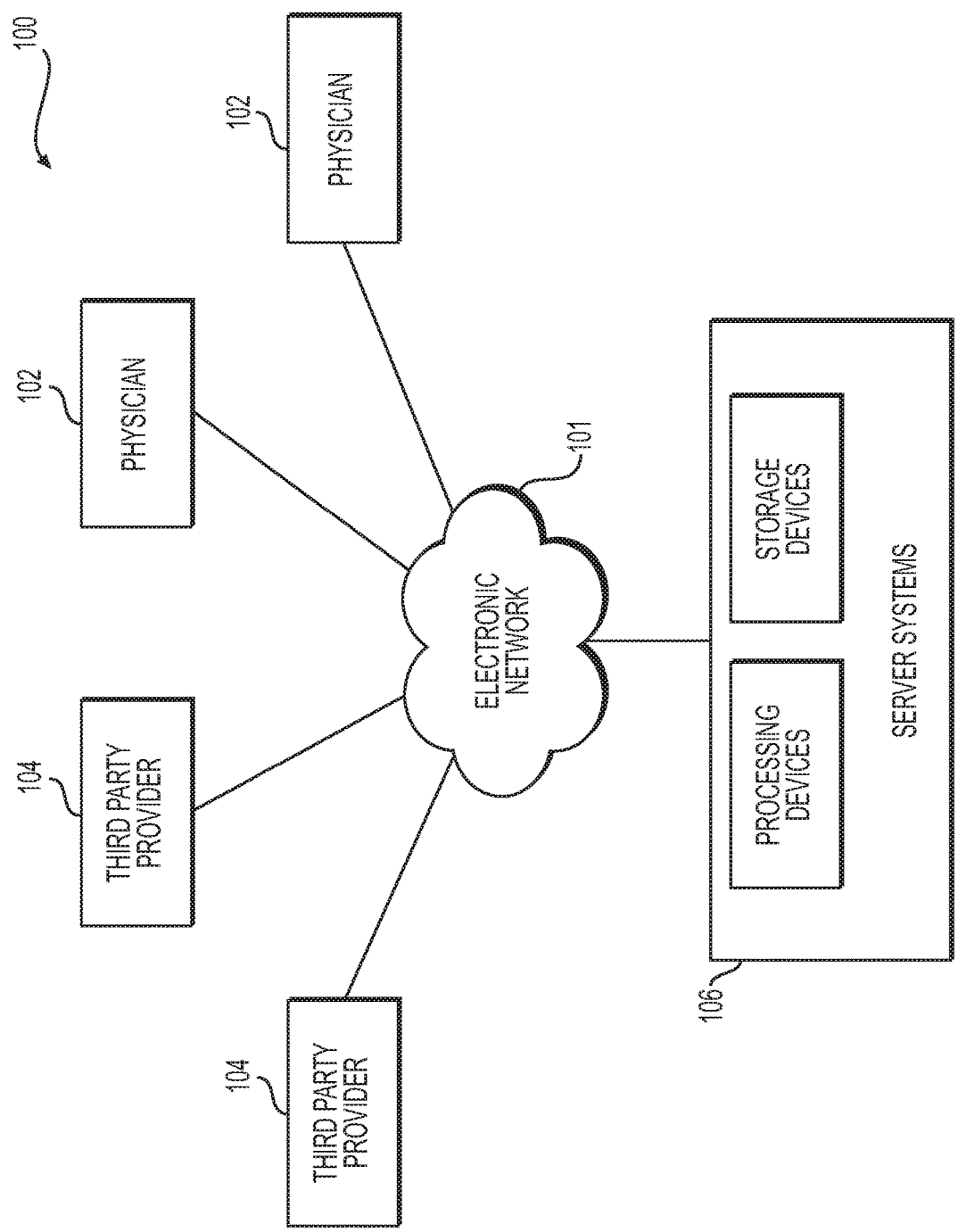
FIG. 1 is a block diagram of an exemplary system and network for creating an interactive tool for determining and displaying a functional relationship between a vascular network and an associated perfused tissue, according to an exemplary embodiment of the present disclosure.

Reference will now be made in detail to the exemplary embodiments of the disclosure, examples of which are illustrated in the accompanying drawings. Wherever possible, the same reference numbers will be used throughout the drawings to refer to the same or like parts.

Disease may be linked to issues with blood supply. Thus, a desire exists for assessments that can show functional relationship(s) between a vascular network and a perfused organ. The present disclosure includes systems and methods for visualizing the functional relationship between a vascular network and a corresponding perfused organ. For example, the present disclosure describes a patient-specific interactive tool to help a user visualize such a functional relationship. The tool may enable a user to visualize blood supply cause-and-effect at a global and/or regional scale, under various treatment and/or physiological conditions. For example, in a scenario involving a coronary vascular network and myocardium associated with the coronary network, a user may select (e.g., click on) a coronary vessel displayed in the tool, and the tool may determine (including displaying by lighting up or coloring) a corresponding portion of myocardial tissue with blood supplied by the coronary vessel selected by the user. In another instance, the user of the previous example may select a portion of myocardial tissue, and the tool may determine and highlight a portion of the coronary vascular network supplying blood to the selected tissue. The display may further include fluid modeling or indicators for tissue characteristics and consequent perfusion/blood flow (e.g., from scar tissue or as an effect of one or more treatments).

Displays may further include suggested vessels or tissue portions to select for displaying functional relationships, e.g., based on received patient images or data associated with a plurality of individuals. For example, patient images may show some issues or irregularities (e.g., scar tissue, stenosis, plaque, etc.). Such issues or irregularities may be detected from imaging, based on contrast intensity or gradients, for instance. Data associated with previous patients or a plurality of individuals may also indicate some portions of vasculature that may be crucial or prone to issues (e.g., embolism). In such cases, displays may include recommendations as to vasculature or tissue for a user to select, in order to pinpoint or troubleshoot possible circulatory issues for a particular patient. In some scenarios, the displays may be presented as a workflow of a series of user interfaces, where most severe or significant trouble areas of vasculature or tissue are recommended for selection first, and less crucial areas of vasculature or tissue are recommended in subsequent user interfaces. Displays may include three-dimensional (3D) or two-dimensional (2D) representations of a patient's vasculature or tissue. Displays may further include histograms or charts, e.g., charts comparing a percentage of tissue affected for various selected vessels, charts comparing a percentage of tissue affected by the geometry of a single selected vessel over time or over various physiological states, charts comparing various treatments in terms of effects of each of the treatments on tissue or vasculature, etc.

The present disclosure may include systems and methods for planning and assessing the effectiveness of vascular related treatments for a patient, for example, by creating an interactive tool for determining and displaying a functional relationship between a vascular network and an associated perfused tissue. In addition, the present disclosure may include systems and methods for assisting in the treatment or relief of one or more vascular conditions, e.g., by suggesting effective treatment(s). This disclosure may also assist in the design and development of surgery or new vascular devices. Further, the disclosure may include embodiments that may be used as patient educational tool(s).

Referring now to the figures, FIG. 1 depicts a block diagram of an exemplary system 100 and network for creating an interactive tool for determining and displaying a functional relationship between a vascular network and an associated perfused tissue, according to an exemplary embodiment. Specifically, FIG. 1 depicts a plurality of physicians 102 and third party providers 104, any of whom may be connected to an electronic network 101, such as the Internet, through one or more computers, servers, and/or handheld mobile devices. Physicians 102 and/or third party providers 104 may create or otherwise obtain images of one or more patients' anatomies. The physicians 102 and/or third party providers 104 may also obtain any combination of patient-specific information, such as age, medical history, blood pressure, blood viscosity, patient activity or exercise level, etc. Physicians 102 and/or third party providers 104 may transmit the anatomical images and/or patient-specific information to server systems 106 over the electronic network 101. Server systems 106 may include storage devices for storing images and data received from physicians 102 and/or third party providers 104. Server systems 106 may also include processing devices for processing images and data stored in the storage devices. For the purposes of the disclosure, "patient" may refer to any individual or person for whom diagnosis or treatment analysis is being performed, or any individual or person associated with the diagnosis or treatment analysis of one or more individuals.

Figure 2A:
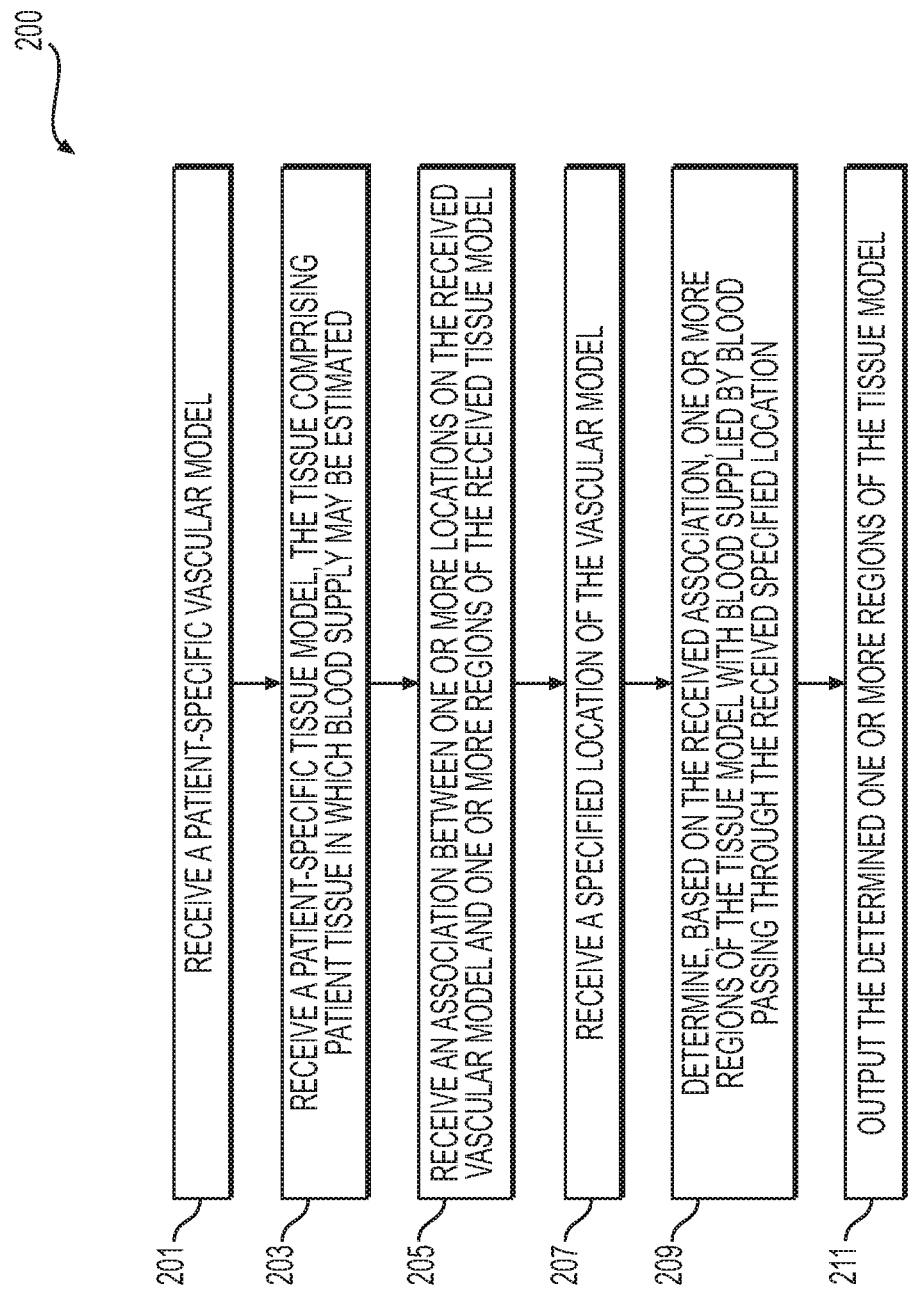
FIG. 2A is a flowchart of an exemplary method of creating an interactive tool for determining and displaying a functional relationship between a vascular network and an associated perfused tissue, according to an exemplary embodiment of the present disclosure.
Figure 2B:
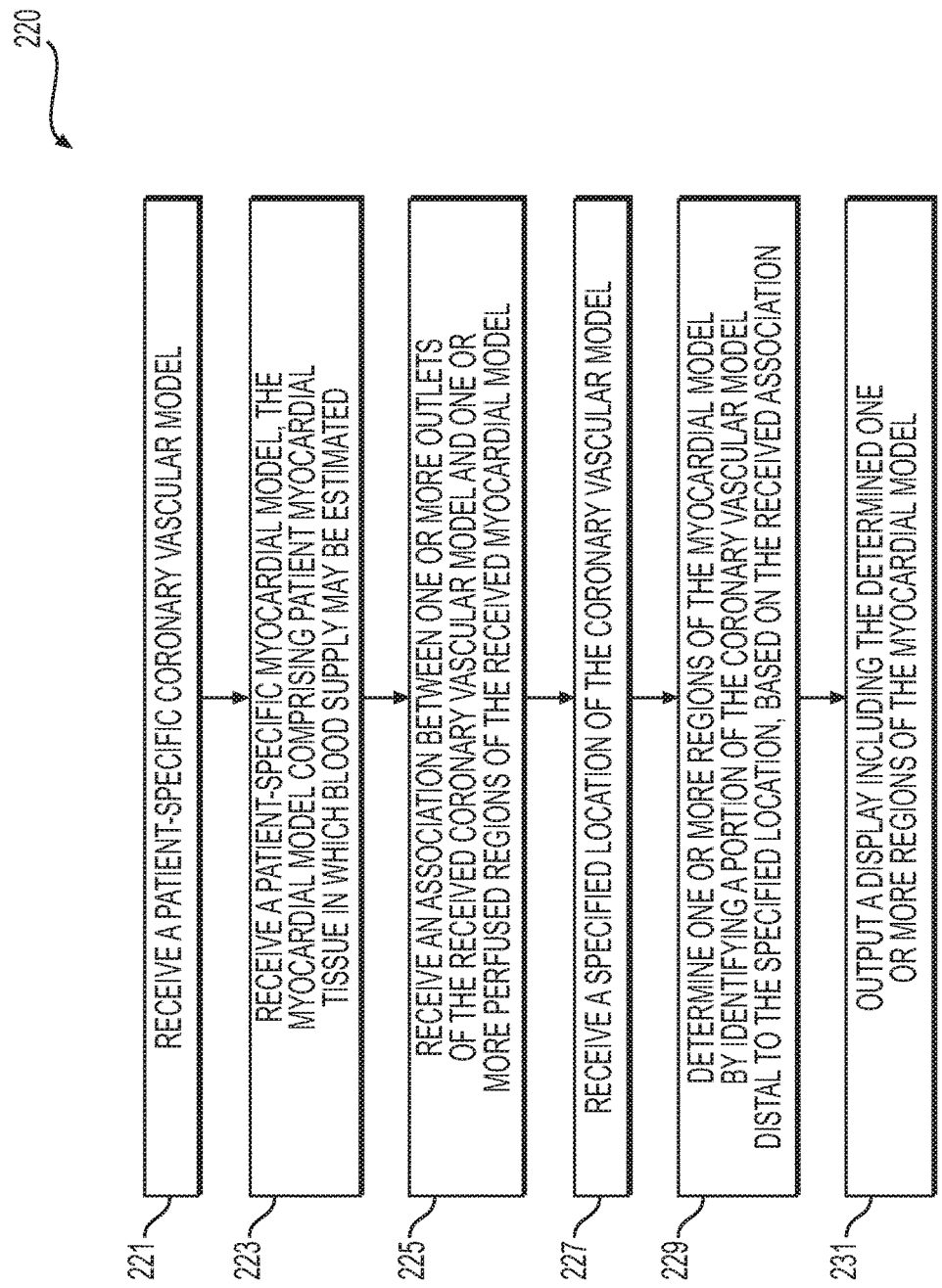
FIG. 2B is a flowchart of an exemplary method of creating an interactive tool for determining and displaying a functional relationship between a coronary vascular network and a myocardium, according to an exemplary embodiment of the present disclosure.
Figure 3A:
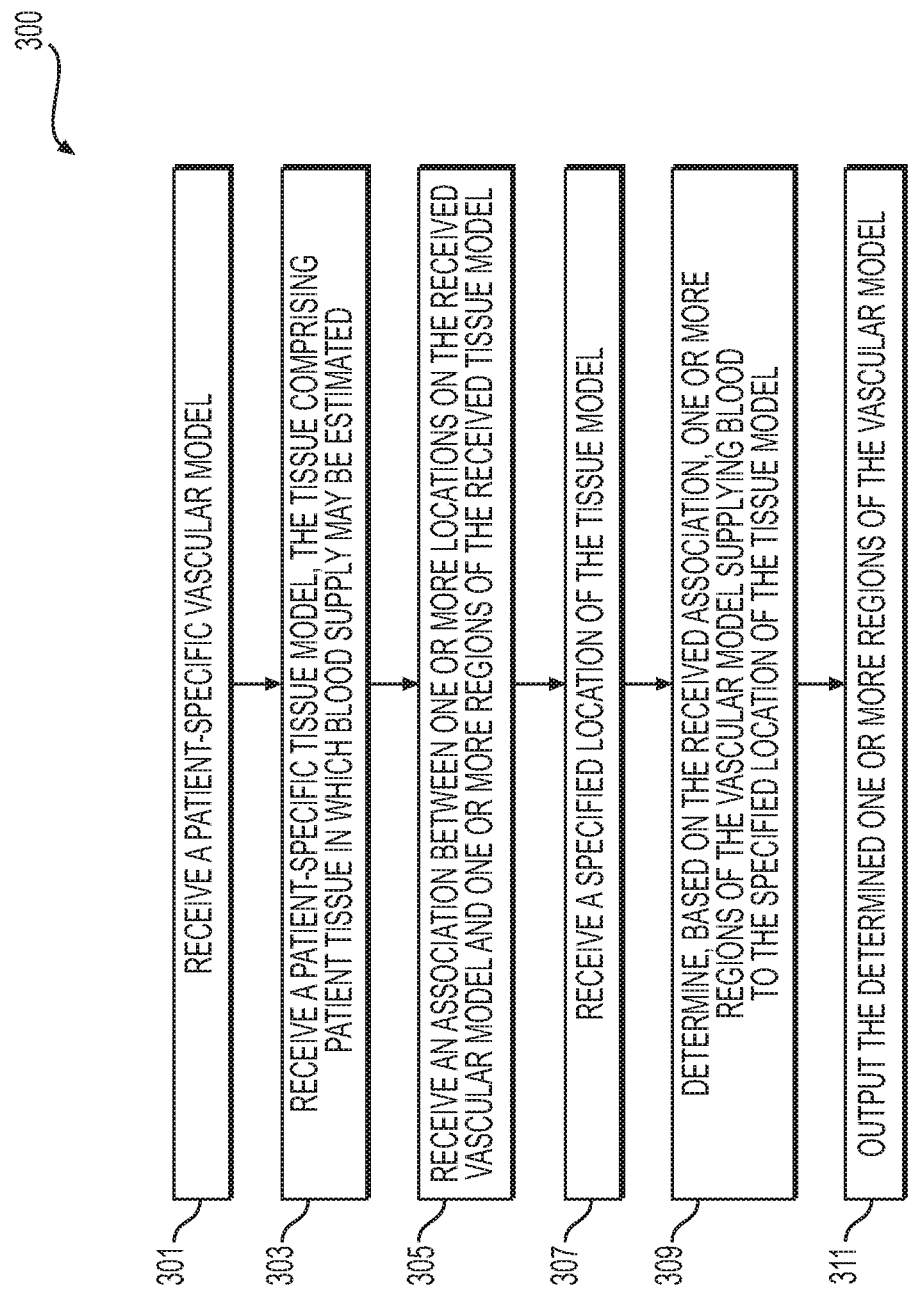
FIG. 3A is a flowchart of another exemplary method of creating an interactive tool for determining and displaying a functional relationship between a vascular network and an associated perfused tissue, according to an exemplary embodiment of the present disclosure.
Figure 3B:
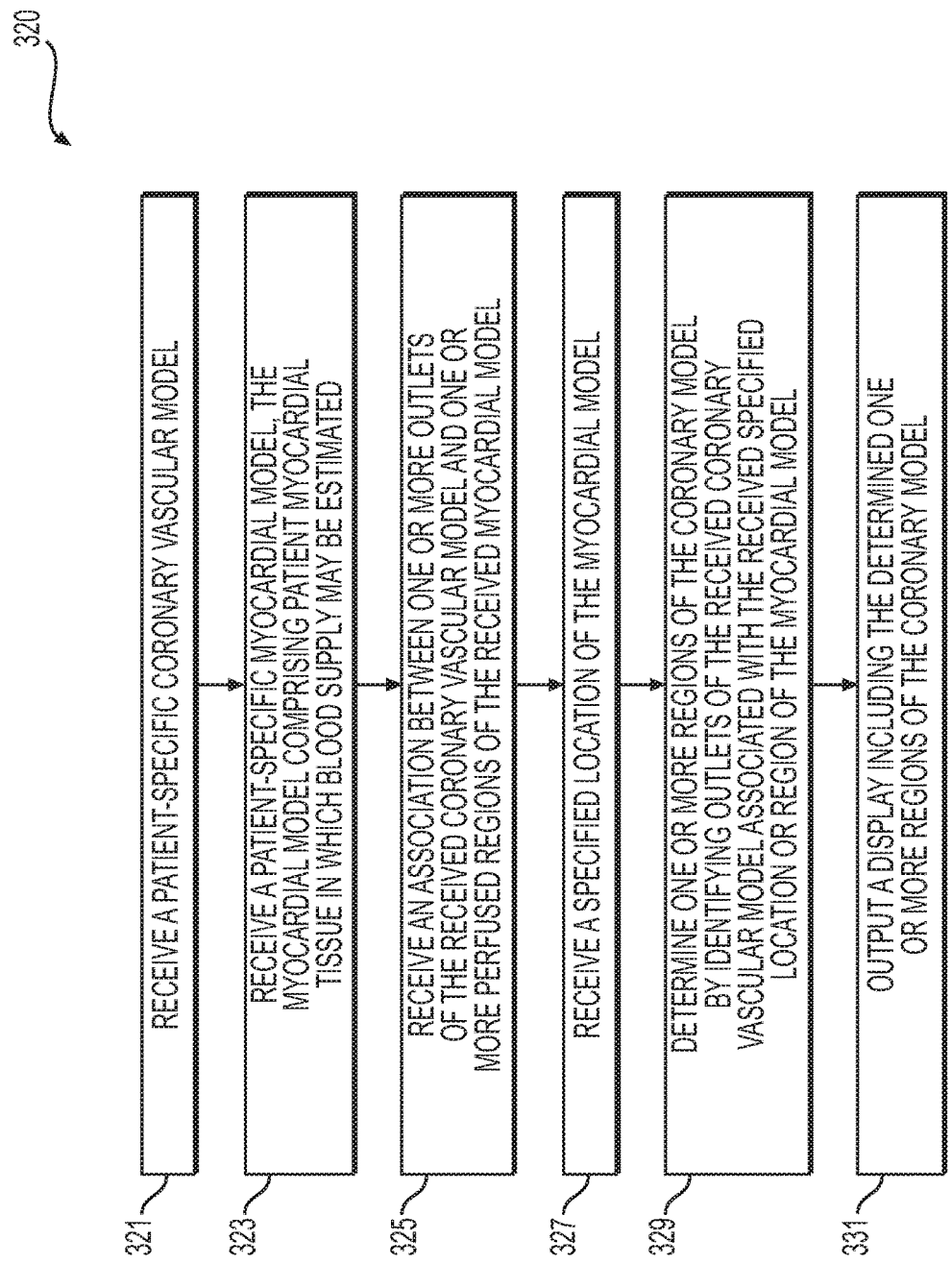
FIG. 3B is a flowchart of another exemplary method of creating an interactive tool for determining and displaying a functional relationship between a coronary vascular network and a myocardium, according to an exemplary embodiment of the present disclosure.
Figure 4A:
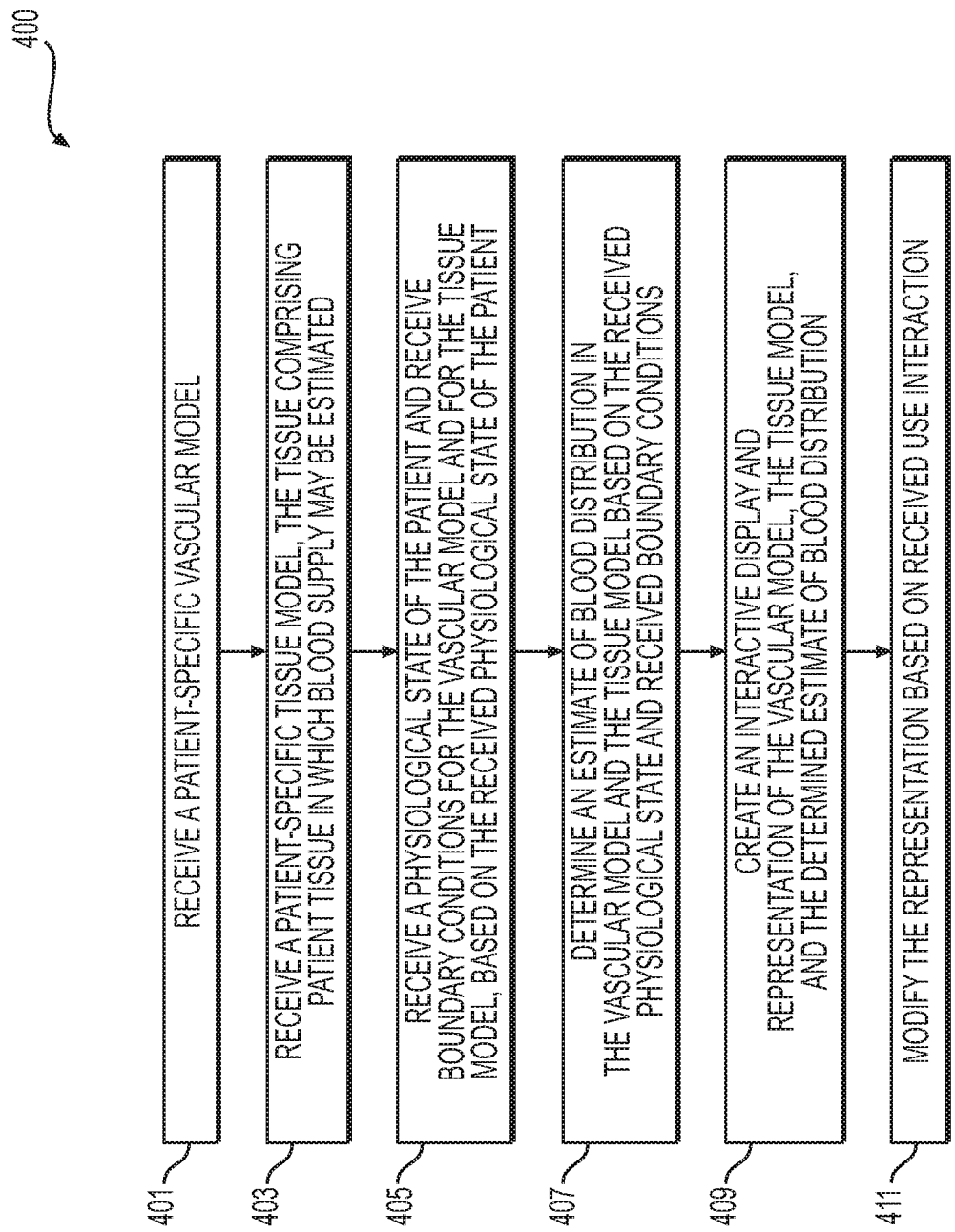
FIG. 4A is a flowchart of an exemplary method of creating an interactive tool for determining and displaying functional information associated with a vascular network and an associated perfused tissue, according to an exemplary embodiment of the present disclosure.
Figure 4B:
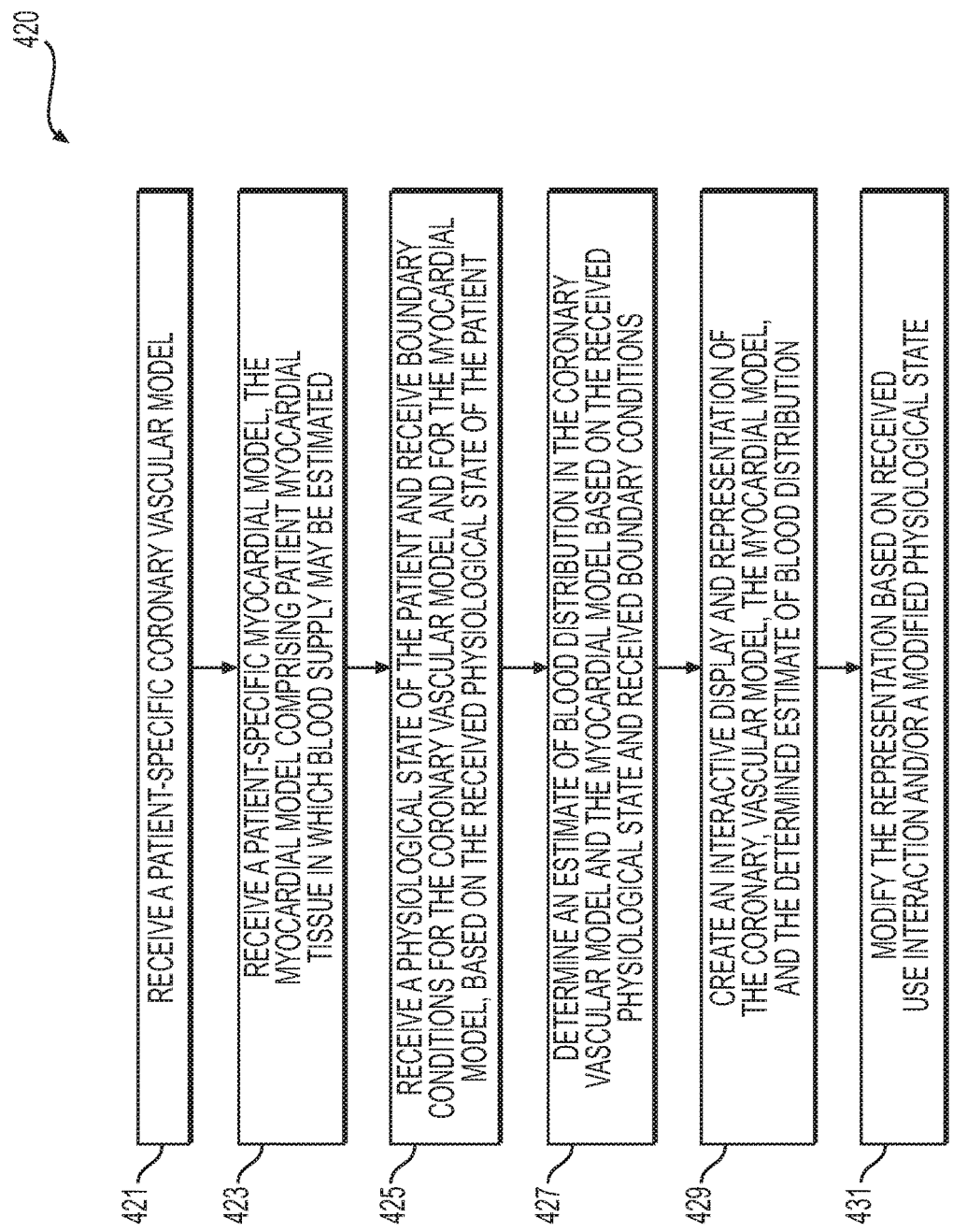
FIG. 4B is a flowchart of an exemplary method of creating an interactive tool for determining and displaying a functional information associated with a coronary vascular network and a myocardium, according to an exemplary embodiment of the present disclosure.
Figure 5A:
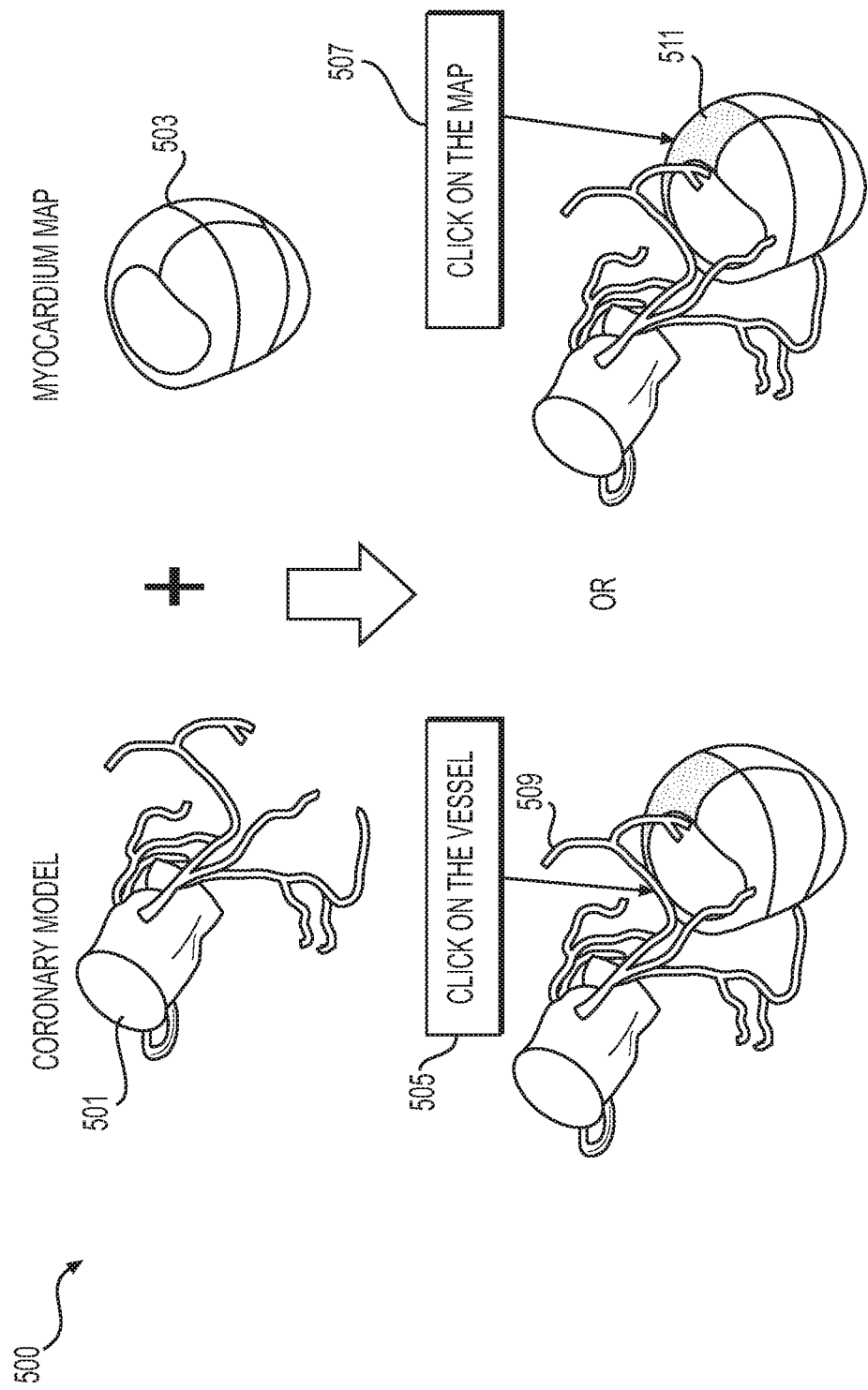
FIGS. 5A and 5B include diagrams of user interfaces configured for displaying a functional relationship(s) between a vascular network and associated perfused tissue, according to exemplary embodiments of the present disclosure.
Figure 5B:
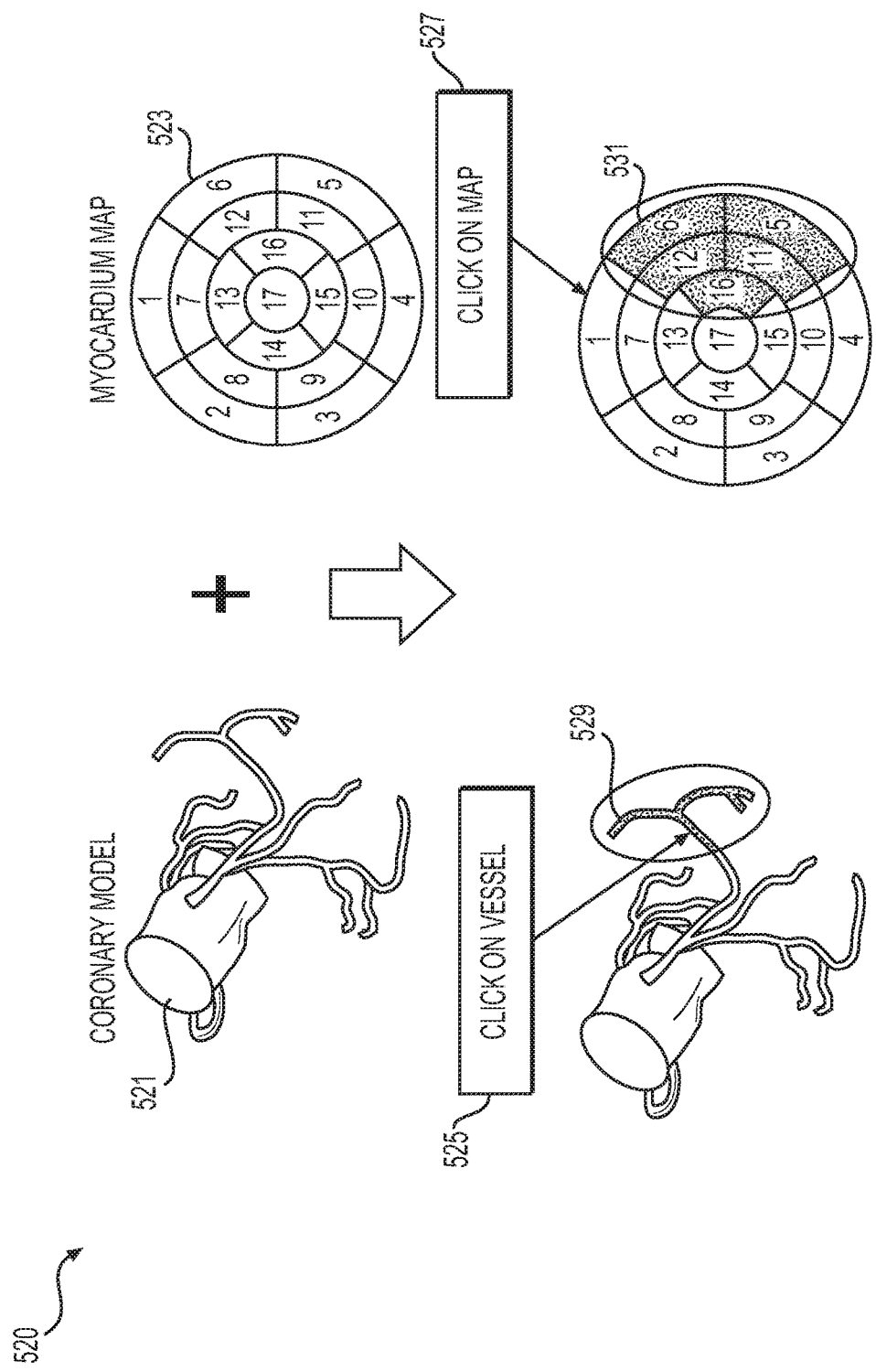

FIG. 2A depicts an exemplary embodiment of creating an interactive tool of a functional relationship between a vascular network and an associated perfused tissue, where a user may select or indicate a portion of vasculature and the tool may determine and show a tissue region perfused by the indicated vasculature. FIG. 3A depicts an exemplary embodiment of creating an interactive tool of a functional relationship between a vascular network and an associated perfused tissue, where a user may select or indicate a tissue region and the tool may determine and show a section of vasculature supplying blood to the indicated tissue region, or a section of vasculature from which the indicated tissue region may receive blood. FIGS. 2B and 3B are detailed embodiments of the methods of FIGS. 2A and 3A, respectively. For example, the method of FIG. 2B may apply the method of FIG. 2A to a coronary vasculature and myocardial tissue. Likewise, the method of FIG. 3B may apply the method of FIG. 3A to a coronary vasculature and myocardial tissue. FIG. 4A depicts an exemplary embodiment of a process for estimating and displaying a blood distribution (e.g., a blood supply estimate) from a vascular network to a target tissue. FIG. 4B depicts a detailed embodiment of the method of FIG. 4A, applying the method of FIG. 4A to a coronary vasculature and myocardial tissue. FIGS. 5A and 5B include exemplary user interfaces produced by the embodiments described in FIGS. 2A-4B.

FIG. 2A is a flowchart of an exemplary method 200 of creating an interactive tool for determining and displaying a functional relationship between a vascular network and an associated perfused tissue, according to an exemplary embodiment. The method of FIG. 2A may be performed by server systems 106, based on information, images, and data received from physicians 102 and/or third party providers 104 over electronic network 101.

In one embodiment, step 201 may include receiving a patient-specific vascular model in an electronic storage medium of the server systems 106. The electronic storage medium may include, for example, a hard drive, network drive, cloud drive, mobile phone, tablet, etc. In one embodiment, the vascular model may be derived from images of the person acquired via one or more available imaging or scanning modalities (e.g., computed tomography (CT) scans and/or magnetic resonance imaging (MRI)). For example, step 201 may include receiving CT and/or MRI images of a person's vasculature. Step 201 may further include generating, from the received images, a patient-specific vascular model for the particular person.

In one embodiment, step 203 may include receiving a patient-specific tissue model in an electronic storage medium of the server systems 106. The tissue of the patient-specific tissue model may include tissue in which blood supply may be estimated. At least a portion of the tissue of the patient-specific tissue model may include target tissue, where the target tissue may include tissue which is being evaluated by a user.

In one embodiment, step 205 may include receiving and/or determining an association between one or more locations on the vascular model (e.g., of step 201) and one or more regions of the tissue model (e.g., the target tissue of the patient-specific tissue model of step 203), where the association may be based on regions of the tissue model that correspond to the one or more locations of the vascular model by way of perfusion territories of the one or more locations of the vascular model. For example, step 205 may include determining a location of the vascular model of step 201 and determining a perfusion territory of the vascular model within the patient-specific tissue model of step 203. Step 205 may include identifying the determined perfusion territory as being associated with the location of the vascular model. Similarly, step 205 may include determining a tissue region of the patient-specific tissue model of step 203 as being within the perfusion territory of a portion of the vascular model of step 201. Step 205 may include receiving and/or determining correspondences between a patient-specific vascular model and a patient-specific tissue model.

In one embodiment, step 207 may include receiving a specified location of the vascular model. The specified location may be received via a user input, e.g., from a user selection of a variety of options. User interaction for selection may include a movement or gesture, movement of a pointer (e.g., a computer mouse), and/or scrolling function across a rendering of the patient-specific model.

In one embodiment, step 209 may include determining, using a processor, one or more regions of tissue supplied by blood passing through the received specified location (e.g., of step 207). For example, the one or more regions of tissue may include at least a portion of target tissue. In one embodiment, step 209 may include determining, from the tissue of the patient-specific tissue model, the one or more regions of tissue supplied by the location of the vascular model specified in step 207. The determination(s) made in step 209 may be based on the associations between the vascular model and the tissue model of step 205.

In one embodiment, step 211 may include outputting the one or more regions of the target tissue supplied by the blood passing through the indicated location. For example, the output of step 211 may include a visual display or an output to an electronic storage medium. In one embodiment, step 211 may further include a visual display or an entry into an electronic storage medium comprising a blood flow characteristic associated with the blood passing through the indicated location. A further step may include determining such a blood flow characteristic, e.g., blood pressure, blood flow rate, blood flow volume, or a metric comprised of a comparison of any of blood flow characteristics, etc. The visual display may include user-interactive features or any sensors known in the art for receiving user input known in the art.

In one embodiment, method 200 may further include treatment analysis. For example, output from step 211 may be used to compare several treatments, where visual displays may be generated for one or more treatments (e.g., various types of medication, exercise regimens, treatment procedures, and/or implants). The effects of each of the treatments can be compared, either simultaneously in one display, or in a series of displays. Furthermore, method 200 may include using the comparison to select a treatment for a patient, either for the person for which the patient-specific anatomic model was constructed (e.g., in step 201) or for another patient (e.g., a patient with characteristics or circumstances similar to the person modeled in step 201).

FIG. 2B is a flowchart of an exemplary method 220 of creating an interactive tool for a functional relationship between a coronary vascular network and a myocardium, according to an exemplary embodiment. The method of FIG. 2B may be performed by server systems 106, based on information, images, and data received from physicians 102 and/or third party providers 104 over electronic network 101.

In one embodiment, step 221 may include receiving a patient-specific coronary model in an electronic storage medium of the server systems 106. The electronic storage medium may include, for example, a hard drive, network drive, cloud drive, mobile phone, tablet, etc. In one embodiment, the coronary model may be obtained via segmentation of an imaging study, e.g., a coronary computed tomography angiography (cCTA) or magnetic resonance imaging (MRI).

In one embodiment, step 223 may include receiving a patient-specific myocardial model in an electronic storage medium of the server systems 106. The tissue of the patient-specific tissue model may include tissue in which blood supply may be estimated. At least a portion of the tissue of the patient-specific tissue model may include target tissue, where the target tissue may include tissue which is being evaluated by a user. This patient-specific myocardial model may be obtained via segmentation of an imaging study, e.g., cCTA or MRI.

In one embodiment, step 225 may include receiving and/or determining an association between one or more locations on the vascular model (e.g., of step 221) and one or more regions of the tissue model (e.g., the target tissue of the patient-specific tissue model of step 223). The association may be based on regions of the tissue model that correspond to the one or more locations of the vascular model by way of perfusion territories of the one or more locations of the vascular model. For example, the association may include matching one or more outlets of the coronary model to corresponding, respective regions of the myocardial model. For instance, step 225 may include matching an outlet of the coronary model to a region of the myocardium, for one or more outlets of the coronary model.

In one embodiment, step 227 may include generating a display of the patient-specific coronary model (e.g., a 3-dimensional display of the coronary model). In one embodiment, step 227 may further include prompting and/or receiving an indicated location of the coronary model (e.g., via user interaction with the 3-dimensional display of the coronary model).

In one embodiment, step 229 may include determining, using a processor, one or more regions of tissue (e.g., myocardial tissue) supplied by blood passing through the received specified location (e.g., of step 227). In one embodiment, step 229 may include identifying a sub-tree of the modeled coronary tree distal to the indicated location (of step 227) and summing together portions of the myocardium territory associated with the indicated location. For example, step 229 may be performed using a union operation. In one such scenario, a union operation may include identifying one or more sub-trees associated with outlets downstream from the indicated location. The union operation may further include merging the identified sub-trees into a single tree. This tree may represent an overall myocardial sub-tree associated with the indicated location.

In one embodiment, step 231 may include outputting the one or more regions of the target tissue supplied by the blood passing through the indicated location. For example, the output of step 231 may include a visual display or an output to an electronic storage medium. For example, step 231 may include displaying the one or more regions on a 3-dimensional model of the myocardium (e.g., by coloring the region) or by coloring a representation of the myocardium (e.g., a 17-segment "bulls-eye" model).

FIG. 3A is a flowchart of an exemplary method 300 of an exemplary method of creating an interactive tool for determining and displaying a functional relationship between a vascular network and an associated perfused tissue, according to an exemplary embodiment. The method of FIG. 3A may be performed by server systems 106, based on information, images, and data received from physicians 102 and/or third party providers 104 over electronic network 101.

In one embodiment, step 301 may include receiving a patient-specific vascular model in an electronic storage medium of the server systems 106. The electronic storage medium may include, for example, a hard drive, network drive, cloud drive, mobile phone, tablet, etc. In one embodiment, the vascular model may be derived from images of the person acquired via one or more available imaging or scanning modalities (e.g., computed tomography (CT) scans and/or magnetic resonance imaging (MRI)). For example, step 301 may include receiving CT and/or MRI images of a person's vasculature. Step 301 may further include generating, from the received images, a patient-specific vascular model for the particular person.

In one embodiment, step 303 may include receiving a patient-specific tissue model in an electronic storage medium of the server systems 106. The tissue of the patient-specific tissue model may include tissue in which blood supply may be estimated. At least a portion of the tissue of the patient-specific tissue model may include target tissue, where the target tissue may include tissue which is being evaluated by a user.

In one embodiment, step 305 may include receiving and/or determining an association between one or more locations on the vascular model (e.g., of step 301) and one or more regions of the tissue model (e.g., the target tissue of the patient-specific tissue model of step 303), where the association may be based on regions of the tissue model that correspond to the one or more locations of the vascular model by way of perfusion territories of the one or more locations of the vascular model. For example, step 305 may include determining a location of the vascular model of step 301 and determining a perfusion territory of the vascular model within the patient-specific tissue model of step 303. Step 305 may include identifying the determined perfusion territory as being associated with the location of the vascular model. Similarly, step 305 may include determining a tissue region of the patient-specific tissue model of step 303 as being within the perfusion territory of a portion of the vascular model of step 301. Step 305 may include receiving and/or determining correspondences between a patient-specific vascular model and a patient-specific tissue model.

In one embodiment, step 307 may include receiving a specified location or region of the tissue model (e.g., a specified location or region of the target tissue). The specified location or region may be received via a user input, e.g., from a user selection of a variety of options. User interaction for selection may include a movement or gesture, movement of a pointer (e.g., a computer mouse), and/or scrolling function across a rendering of the patient-specific model.

In one embodiment, step 309 may include determining, using a processor, one or more regions of the vascular model supplying blood to the received specified location or region of the tissue model (e.g., of step 307). The determination(s) made in step 309 may be based on the associations between the vascular model and the tissue model of step 305.

In one embodiment, step 311 may include outputting the one or more regions of the vascular model supplying blood to the received specified location or region (e.g., of step 307). For example, the output of step 311 may include a visual display or an output to an electronic storage medium. In one embodiment, step 311 may further include a visual display or an entry into an electronic storage medium comprising a blood flow characteristic associated with the blood passing through the indicated location or region of tissue. A further step may include determining such a blood flow characteristic, e.g., blood pressure, blood flow rate, blood flow volume, or a metric comprised of a comparison of any of blood flow characteristics, etc. The visual display may include user-interactive features or any sensors known in the art for receiving user input known in the art.

In one embodiment, method 300 may further include treatment analysis. For example, output from step 311 may be used to compare several treatments, where visual displays may be generated for one or more treatments (e.g., various types of medication, exercise regimens, treatment procedures, and/or implants). The effects of each of the treatments can be compared, either simultaneously in one display, or in a series of displays. Furthermore, method 300 may include using the comparison to select a treatment for a patient, either for the person for which the patient-specific anatomic model was constructed (e.g., in step 301) or for another patient (e.g., a patient with characteristics or circumstances similar to the person modeled in step 301).

FIG. 3B is a flowchart of an exemplary method 320 of creating an interactive tool for a functional relationship between a coronary vascular network and a myocardium, according to an exemplary embodiment. The method of FIG. 3B may be performed by server systems 106, based on information, images, and data received from physicians 102 and/or third party providers 104 over electronic network 101.

In one embodiment, step 321 may include receiving a patient-specific coronary model as a patient-specific vascular model in an electronic storage medium of the server systems 106. The electronic storage medium may include, for example, a hard drive, network drive, cloud drive, mobile phone, tablet, etc. In one embodiment, the coronary model may be obtained via segmentation of an imaging study, e.g., a coronary computed tomography angiography (cCTA) or magnetic resonance imaging (MRI).

In one embodiment, step 323 may include receiving a patient-specific myocardial model as a patient-specific tissue model in an electronic storage medium of the server systems 106. The tissue of the patient-specific myocardial model may include tissue in which blood supply may be estimated. At least a portion of the tissue of the patient-specific myocardial model may include target tissue, where the target tissue may include tissue which is being evaluated by a user. This patient-specific myocardial model may be obtained via segmentation of an imaging study, e.g., cCTA or MRI.

In one embodiment, step 325 may include receiving and/or determining an association between one or more locations on the patient-specific coronary vascular model (e.g., of step 321) and one or more regions of the patient-specific myocardial model (e.g., the target tissue of the patient-specific tissue model of step 323). The association may be based on regions of the myocardial model that correspond to the one or more locations of the coronary model by way of perfusion territories of the one or more locations of the vascular model. For example, the association may include matching one or more outlets of the coronary model to corresponding, respective regions of the myocardial model. For instance, step 325 may include matching an outlet of the coronary model to a region of the myocardium, for one or more outlets of the coronary model.

In one embodiment, step 327 may include generating a display of the patient-specific myocardial model (e.g., a 3-dimensional display of the myocardial model). Alternately or in addition, step 327 may include generating a display including a representation of the patient's myocardium as "bulls-eye" plot (e.g., a 17-segment "bulls-eye" plot). In one embodiment, step 327 may further include prompting and/or receiving an indicated location or region of the myocardial model (e.g., via user interaction with the 3-dimensional display of the coronary model, with a "bulls-eye plot," etc.).

In one embodiment, step 329 may include determining, using a processor, one or more regions of the coronary model supplying blood to the received specified location or region of the myocardial model (e.g., of step 327). In one embodiment, step 329 may include identifying a sub-tree of the modeled coronary tree defined by tracing the indicated location or region through associated outlets of the patient's modeled aortic ostium. This tracing may be performed by following the vessel centerline downstream toward the vessel outlets. Following the direction toward the vessel outlets of the coronary model may be determined in multiple ways, for example, by moving along the coronary model in the direction opposite the aorta connection, by moving in the direction of anatomically smaller vessels of the coronary model, by moving in the direction opposite of a bifurcation of the coronary model that contains a larger vessel, or by moving in the direction of computed (or measured) blood flow of the coronary model (e.g., by following a pressure gradient downward or a flow direction).

In one embodiment, step 331 may include outputting the one or more regions of the coronary model (e.g., the portion of the coronary tree of the coronary model) supplying blood to the indicated location or region. For example, the output of step 331 may include a visual display (e.g., a 3-dimensional representation of the coronary model) or an output to an electronic storage medium.

FIGS. 4A and 4B depict exemplary methods for displaying functional information including blood supply/blood distribution either from a selected vascular network to a tissue region, or received by a selected tissue region from an associated vascular network providing blood to that selected tissue region. FIG. 4A depicts an exemplary embodiment of a process for estimating and displaying a blood distribution (e.g., a blood supply estimate) from a vascular network to a target tissue. FIG. 4B depicts a detailed embodiment of the method of FIG. 4A, applying the method of FIG. 4A to a coronary vasculature and myocardial tissue.

FIG. 4A is a flowchart of an exemplary method 400 of an exemplary method of creating an interactive tool for determining and displaying a functional relationship between a vascular network and an associated perfused tissue, according to an exemplary embodiment. The method of FIG. 4A may be performed by server systems 106, based on information, images, and data received from physicians 102 and/or third party providers 104 over electronic network 101.

In one embodiment, step 401 may include receiving a patient-specific vascular model in an electronic storage medium of the server systems 106. The electronic storage medium may include, for example, a hard drive, network drive, cloud drive, mobile phone, tablet, etc. In one embodiment, the vascular model may be derived from images of the person acquired via one or more available imaging or scanning modalities (e.g., computed tomography (CT) scans and/or magnetic resonance imaging (MRI)). For example, step 401 may include receiving CT and/or MRI images of a person's vasculature. Step 401 may further include generating, from the received images, a patient-specific vascular model for the particular person.

In one embodiment, step 403 may include receiving a patient-specific tissue model in an electronic storage medium of the server systems 106. The tissue of the patient-specific tissue model may include tissue in which blood supply may be estimated. At least a portion of the tissue of the patient-specific tissue model may include target tissue, where the target tissue may include tissue which is being evaluated by a user.

In one embodiment, step 405 may include receiving and/or determining a physiological state of the patient and boundary conditions for the patient-specific vascular model and/or the patient-specific tissue model.

In one embodiment, step 407 may include determining, using a processor, an estimate of a blood distribution in the vascular network (of at least a portion of the patient-specific vascular model) and the target tissue (of at least a portion of the patient-specific tissue model). Exemplary processors may include: a laptop, desktop, cloud computing architecture, GPU, DSP, mobile phone, tablet, etc. In one embodiment, the blood distribution may be based on the received models and the received physiological state, including the boundary conditions (e.g., of step 405). The blood distribution may include a blood supply, e.g., an estimate expressed as blood pressure, blood flow, blood speed, blood flow rate, etc. The blood distribution may be estimated using computational fluid dynamics with the determined boundary conditions (e.g., a 3D model, reduced order model, 1D model, or 0D model). Alternatively or in addition, the blood distribution may be estimated using a statistical or machine learning technique from example data.

In one embodiment, step 409 may include outputting a representation and/or visual display of the patient-specific vascular model and/or the patient-specific tissue model to an electronic storage medium or a user display (e.g., a monitor, mobile phone, tablet, etc.). The representation may comprise a model interface.

In one embodiment, step 411 may include projecting functional information (e.g., the blood distribution estimate of step 407) onto the output of step 409. In one embodiment, the model interface may include features for receiving and/or prompting user interaction. In one embodiment, step 411 may include displaying a blood supply estimate inside or near a user selection of at least a portion of a vascular network. Alternately or in addition, step 411 may include displaying a blood supply estimate inside or near a target tissue supplied by a user selected portion of a vascular network. In one embodiment, step 411 may include displaying a blood supply estimate inside or near a user selection of at least a portion of a target tissue region. Alternately or in addition, step 411 may include displaying a blood supply estimate inside or near a vascular network responsible for supplying a user selected portion of target tissue.

User selection may include a movement or gesture, movement of a pointer (e.g., a computer mouse), and/or scrolling function across the model interface. In one embodiment, display(s) created in steps 409 and 411 may include outlining and/or indicating user selections of the patient-specific vascular model and/or the patient-specific tissue model. For example, a user may trace a target tissue on a screen showing a display of the patient-specific tissue model. Steps 409 and 411 may include showing a colored line outlining the traced tissue region, with corresponding functional information of the tissue shown alongside or within the colored line. Relationships between the projected functional information and visual representations of the models may be conveyed via color coordination, overlays of functional information over selected area(s) of the model(s), proximity between displayed functional information and selected area(s) of model(s), etc.

In one embodiment, step 413 may include determining and/or receiving a modification, e.g., a modification to the physiological state (e.g., of step 405). For example, step 413 may include prompting a user to modify a patient physiological state and/or determining a physiological state change/new physiological state of the patient. Step 413 may further include determining and/or receiving boundary conditions associated with the changed physiological state and updating renderings created in steps 409 and 411. In other or additional embodiments, step 413 may include modifications to the patient models, including modifications for changes over time (e.g., aging and/or plaque progression) and/or for simulations of medical treatment (e.g., stent insertion or bypass procedures).

In one embodiment, steps 409 and 411 may be performed again, taking into consideration modification(s) received or determined in step 413. For example, functional information and/or model interface(s) may be regenerated and/or updated to incorporate the modifications. For instance, the geometry of a patient-specific vascular model may be modified to model a stent insertion. Any change to boundary conditions in light of the changed geometry may be applied to assessment of functional information (e.g., blood flow rate through the modified geometry of the patient-specific vascular model) and/or consequent blood supply to tissue associated with the modified portion of the patient-specific vascular model. Such changes in model geometry and functional information may be displayed with steps 409 and 411. In some embodiments, steps 409 and 411 may further include simultaneous displays of model interfaces. For example, repeating steps 409 and 411 may produce side-by-side comparisons and/or overlays of patient-specific models and/or functional information at various physiological states, geometric configurations, points in time, etc.

FIG. 4B is a flowchart of an exemplary method 420 of creating an interactive tool for a functional relationship between a coronary vascular network and a myocardium, according to an exemplary embodiment. The method of FIG. 4B may be performed by server systems 106, based on information, images, and data received from physicians 102 and/or third party providers 104 over electronic network 101.

In one embodiment, step 421 may include receiving a patient-specific cardiovascular model in an electronic storage medium of the server systems 106. The electronic storage medium may include, for example, a hard drive, network drive, cloud drive, mobile phone, tablet, etc. The cardiovascular model may include large coronary vessels (e.g., obtained via imaging including CT or MR) and/or including microvasculture perfusing tissue. The microvasculature may be measured or simulated (e.g., via constrained constructive optimization or other similar methods). The cardiovascular model may include arteries, veins, or a combination thereof. In one embodiment, the coronary model may be obtained via segmentation of an imaging study, e.g., a coronary computed tomography angiography (cCTA) or magnetic resonance imaging (MRI), or extracted from a medical imaging scan (e.g., CT or MR).

In one embodiment, step 423 may include receiving a patient-specific myocardial model in an electronic storage medium of the server systems 106. The tissue of the patient-specific tissue model may include tissue in which blood supply may be estimated. At least a portion of the tissue of the patient-specific tissue model may include target tissue, where the target tissue may include tissue which is being evaluated by a user. The myocardial model may include model(s) of the patient's epicardium, atrial wall, etc. This patient-specific myocardial model may be obtained via segmentation of an imaging study, e.g., cCTA or MRI, or extracted from a medical imaging scan (e.g., CT or MR).

In one embodiment, step 425 may include receiving and/or determining a physiological state of the patient and/or cardiac phase of the cardiovascular model. The physiological state may include, for example, exercise state, resting state, hyperemic state, etc. Cardiac phases may refer to diastole, systole, etc. Step 425 may further include receiving and/or determining boundary conditions for the patient-specific cardiovascular model and/or the myocardial model, based on the received/determined physiological state or cardiac phase.

In one embodiment, step 427 may include determining, using a processor, an estimate of a blood supply in the patient's coronary vessels and myocardium based on the patient-specific cardiovascular model (e.g., of step 421), the patient-specific myocardial model (e.g., of step 423), and the received/determined boundary conditions (e.g., of step 425). Exemplary processors may include: a laptop, desktop, cloud computing architecture, graphics processing unit (GPU), digital signal processor (DSP), mobile phone, tablet, etc. In one embodiment, estimating the blood supply may include determining blood flow in the cardiovascular model, e.g., using a patient-specific estimation of blood flow in the coronary vessels. For example, step 427 may include estimating blood flow demand (e.g., based on the myocardial mass of the myocardial model, of the patient, the total vascular volume of the patient's coronary vessels, or the total vascular volume of the cardiovascular model). Estimating blood flow on the basis of blood flow demand may further be performed using 3D computational fluid dynamics, a reduced order model, and/or using a database (e.g., via machine learning).

In one embodiment, estimating myocardium perfusion may include using a patient-specific estimation of blood advection-diffusion in the myocardium based on cardiovascular supply (e.g., blood supply to the heart, blood supply to the aorta, or some known blood pressure in the vessel tree). Estimating myocardium perfusion may also employ 3D computational fluid dynamics, a reduced order model, and/or using a database (e.g., via machine learning).

In one embodiment, step 429 may include outputting a representation and/or visual display of the patient-specific vascular model and/or the patient-specific tissue model to an electronic storage medium or a user display (e.g., a monitor, mobile phone, tablet, etc.). The representation may comprise a model interface. Model interfaces may include 3D geometrical model(s) (e.g., a triangulated surface mesh) of the cardiovascular model and/or the myocardial model. Alternately or in addition, the model interfaces may include 2D representation(s) of the cardiovascular model and/or the myocardial model, e.g., a projection of the cardiovascular model and/or a projection or "bull's-eye" plot of the myocardial model).

In one embodiment, step 431 may include projecting functional information (e.g., the blood supply estimate of step 427) onto the output of step 429. In one embodiment, the model interface may include features for receiving and/or prompting user interaction. In one embodiment, step 431 may include displaying a blood supply estimate inside or near a user selection of at least a portion of the displayed cardiovascular network. Alternately or in addition, step 431 may include displaying a blood supply estimate inside or near a target myocardial tissue supplied by a user selected portion of a displayed cardiovascular network. In one embodiment, step 431 may include displaying a blood supply estimate inside or near a user selection of at least a portion of a target myocardial tissue region. Alternately or in addition, step 431 may include displaying a blood supply estimate inside or near a displayed cardiovascular network responsible for supplying a user selected portion of target myocardial tissue.

In one embodiment, step 433 may include determining and/or receiving a modification, e.g., a modification to the physiological state (e.g., of step 425). For example, step 413 may include prompting a user to modify a patient physiological state and/or determining a physiological state change/new physiological state of the patient. Step 433 may further include determining and/or receiving boundary conditions associated with the changed physiological state and updating renderings created in steps 429 and 431. In other or additional embodiments, step 433 may include modifications to the patient models, including modifications for changes over time (e.g., aging and/or plaque progression) and/or for simulations of medical treatment (e.g., drugs, percutaneous coronary intervention (PCI), coronary artery bypass graft (CABG), myocardium ablation, etc.).

In one embodiment, steps 429 and 431 may be performed again, taking into consideration modification(s) received or determined in step 433. For example, functional information and/or model interface(s) may be regenerated and/or updated to incorporate the modifications. In some embodiments, steps 429 and 431 may further include simultaneous displays of model interfaces as previously described for method 400 of FIG. 4A.

FIGS. 5A and 5B include diagrams of user interfaces displaying functional relationship(s) between a vascular network and associated perfused tissue, according to an exemplary embodiment of the present disclosure.

In particular, FIG. 5A depicts a user interface 500 showing a three-dimensional coronary model 501 and a three-dimensional myocardial model 503, according to an exemplary embodiment of the present disclosure. The user interface 500 may include a vascular model prompt 505 (e.g., prompting a user to select a location of the coronary model 501). Alternately or in addition, the user interface 500 may include a tissue model prompt 507 (e.g., prompting a user to select a region of the myocardial model 503). In one embodiment, the user interface 500 may include a color change or other visual indication (e.g., shading, outlining, overlay, etc.) corresponding to a selected location or region. In one embodiment, the user interface 500 may display a tissue region 509 corresponding to a user response to the vascular model prompt 505. Alternately or in addition, the user interface 500 may display at least one vessel segment 511 corresponding to a user response to the tissue model prompt 507.

FIG. 5B depicts a user interface 520 showing a three-dimensional coronary model 521 and a two dimensional myocardial model (e.g., a "bull's-eye" plot 523), according to an exemplary embodiment of the present disclosure. The user interface 520 may include a vascular model prompt 525 (e.g., prompting a user to select a location of the coronary model 521). Alternately or in addition, the user interface 520 may include a tissue model prompt 527 (e.g., prompting a user to select a region of the plot 523). In one embodiment, the user interface 520 may include a color change or other visual indication (e.g., shading, outlining, overlay, etc.) corresponding to a selected location or region. Alternately or in addition, the user interface 520 may display at least one vessel segment 529 corresponding to a user response to the tissue model prompt 527. In one embodiment, the user interface 520 may display a tissue region 531 corresponding to a user response to the vascular model prompt 525.

The present disclosure may also apply to carotid or cerebral vascular networks perfusion the brain, peripheral vasculature perusing muscle, renal vasculature supplying kidney(s), visceral vasculature supplying bowels, a liver, or a spleen, etc.

Thus, the present disclosure advantageously describes systems and methods for visualizing the functional relationship between a vascular network and a corresponding perfused organ. For example, the systems and methods describe a tool that displays a corresponding tissue region upon receiving user selection of a vessel segment, and/or a corresponding vasculature upon receiving user selection of a tissue region. Such displays show patient-specific blood supply cause-and-effect at a global and/or regional scale, and under various treatment and/or physiological conditions. The display(s) further includes fluid modeling or indicators for tissue characteristics and consequent perfusion/blood flow (e.g., from scar tissue or as an effect of one or more treatments). The described systems and methods may improve treatment planning for the relief of one or more vascular conditions.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A computer-implemented method for displaying information of a functional relationship between a vasculature and a perfused tissue, the method comprising:
   receiving a patient-specific vascular model of a patient's anatomy;
   receiving a patient-specific tissue model of the patient's anatomy, the patient-specific tissue model describing a tissue supplied at least in part with blood through a vasculature described by the patient-specific vascular model;
   generating a user interface comprising a display of at least a portion of the patient-specific vascular model and a display of at least a portion of the patient-specific tissue model;
   receiving, via the user interface, a selection indicating a portion of a first model, the first model being one of the patient-specific vascular model and the patient-specific tissue model, the indicated portion of the first model having a blood supply relationship with an associated portion of a second model, the second model being another of the patient-specific vascular model and the patient-specific tissue model; and
   upon receiving the selection of the portion of the first model, displaying, in the user interface:
      the portion of the second model in a manner indicating that the associated portion of the second model has the blood supply relationship with the indicated portion of the first model, or
      a blood supply estimate inside or near one of the indicated portion of the first model and the associated portion of the second model.

2. The computer-implemented method of claim 1, wherein
   the first model is the patient-specific vascular model,
   the indicated portion of the first model represents a portion of the vasculature,
   the second model is the patient-specific tissue model, and
   the blood supply relationship is a relationship in which the associated portion of the second model represents a portion of the tissue supplied by blood passing through the portion of the vasculature.

3. The computer-implemented method of claim 2, wherein
   the displaying displays the associated portion of the second model in a manner indicating that the associated portion of the second model has the blood supply relationship with the indicated portion of the first model, and
   the associated portion of the second model is a region of a geometrical model of the patient-specific tissue model or a region of a bulls-eye model of the patient-specific tissue model.

4. The computer-implemented method of claim 2, wherein
   the displaying displays the blood supply estimate inside or near the indicated portion of the first model,
   the blood supply estimate is an estimate of a blood supply in the vasculature, and
   the method comprises, prior to the displaying, determining the estimate of blood supply in the vasculature based on the patient-specific vascular model.

5. The computer-implemented method of claim 2, wherein
   the displaying displays the blood supply estimate inside or near the associated portion of the second model,
   the blood supply estimate is an estimate of a blood supply in the tissue, and
   the method comprises, prior to the displaying, determining the estimate of blood supply in the tissue based on the patient-specific tissue model.

6. The computer-implemented method of claim 1, wherein
   the first model is the patient-specific tissue model,
   the indicated portion of the first model represents a portion of the tissue,
   the second model is the patient-specific vascular model, and
   the blood supply relationship is a relationship in which the associated portion of the second model represents a location of the vasculature that supplies blood to the portion of the tissue.

7. The computer-implemented method of claim 6, wherein
   the displaying displays the associated portion of the second model in a manner indicating that the associated portion of the second model has the blood supply relationship with the indicated portion of the first model, and
   the indicated portion of the first model is a region of a geometrical model of the patient-specific tissue model or a region of a bulls-eye model of the patient-specific tissue model.

8. The computer-implemented method of claim 1, wherein
   the displaying displays the blood supply estimate inside or near the one of the indicated portion of the first model and the associated portion of the second model, and
   the blood supply estimate is a blood pressure, a blood flow, a blood flow rate, or a blood speed.

9. A system for displaying information of a functional relationship between a vasculature and a perfused tissue, the system comprising:
   at least one data storage device storing instructions for creating an interactive tool for determining and displaying a functional relationship between a vascular network and an associated perfused tissue; and
   at least one processor configured to execute the instructions to perform a method including:
      receiving a patient-specific vascular model of a patient's anatomy;
      receiving a patient-specific tissue model of the patient's anatomy, the patient-specific tissue model describing a tissue supplied at least in part with blood through a vasculature described by the patient-specific vascular model;
      generating a user interface comprising a display of at least a portion of the patient-specific vascular model and a display of at least a portion of the patient-specific tissue model;
      receiving, via the user interface, a selection indicating a portion of a first model, the first model being one of the patient-specific vascular model and the patient-specific tissue model, the indicated portion of the first model having a blood supply relationship with an associated portion of a second model, the second model being another of the patient-specific vascular model and the patient-specific tissue model; and upon receiving the selection of the portion of the first model, displaying, in the user interface:
the portion of the second model in a manner indicating that the associated portion of the second model has the blood supply relationship with the indicated portion of the first model, or
a blood supply estimate inside or near one of the indicated portion of the first model and the associated portion of the second model.

10. The system of claim 9, wherein
the first model is the patient-specific vascular model,
the indicated portion of the first model represents a portion of the vasculature,
the second model is the patient-specific tissue model, and
the blood supply relationship is a relationship in which the associated portion of the second model represents a portion of the tissue supplied by blood passing through the portion of the vasculature.

11. The system of claim 10, wherein
the displaying displays the associated portion of the second model in a manner indicating that the associated portion of the second model has the blood supply relationship with the indicated portion of the first model, and
the associated portion of the second model is a region of a geometrical model of the patient-specific tissue model or a region of a bulls-eye model of the patient-specific tissue model.

12. The system of claim 10, wherein
the displaying displays the blood supply estimate inside or near the indicated portion of the first model,
the blood supply estimate is an estimate of a blood supply in the vasculature, and
the method comprises, prior to the displaying, determining the estimate of blood supply in the vasculature based on the patient-specific vascular model.

13. The system of claim 10, wherein
the displaying displays the blood supply estimate inside or near the associated portion of the second model,
the blood supply estimate is an estimate of a blood supply in the tissue, and
the method comprises, prior to the displaying, determining the estimate of blood supply in the tissue based on the patient-specific tissue model.

14. The system of claim 10, wherein
the first model is the patient-specific tissue model,
the indicated portion of the first model represents a portion of the tissue,
the second model is the patient-specific vascular model, and
the blood supply relationship is a relationship in which the associated portion of the second model represents a location of the vasculature that supplies blood to the portion of the tissue.

15. A non-transitory computer-readable medium storing operations for displaying information of a functional relationship between a vasculature and a perfused tissue, the operations comprising:
receiving a patient-specific vascular model of a patient's anatomy;
receiving a patient-specific tissue model of the patient's anatomy, the patient-specific tissue model describing a tissue supplied at least in part with blood through a vasculature described by the patient-specific vascular model;
generating a user interface comprising a display of at least a portion of the patient-specific vascular model and a display of at least a portion of the patient-specific tissue model;
receiving, via the user interface, a selection indicating a portion of a first model, the first model being one of the patient-specific vascular model and the patient-specific tissue model, the indicated portion of the first model having a blood supply relationship with an associated portion of a second model, the second model being another of the patient-specific vascular model and the patient-specific tissue model; and
upon receiving the selection of the portion of the first model, displaying, in the user interface:
the portion of the second model in a manner indicating that the associated portion of the second model has the blood supply relationship with the indicated portion of the first model, or
a blood supply estimate inside or near one of the indicated portion of the first model and the associated portion of the second model.

16. The computer-readable medium of claim 15, wherein
the first model is the patient-specific vascular model,
the indicated portion of the first model represents a portion of the vasculature,
the second model is the patient-specific tissue model, and
the blood supply relationship is a relationship in which the associated portion of the second model represents a portion of the tissue supplied by blood passing through the portion of the vasculature.

17. The computer-readable medium of claim 16, wherein
the displaying displays the associated portion of the second model in a manner indicating that the associated portion of the second model has the blood supply relationship with the indicated portion of the first model, and
the associated portion of the second model is a region of a geometrical model of the patient-specific tissue model or a region of a bulls-eye model of the patient-specific tissue model.

18. The computer-readable medium of claim 16, wherein
the displaying displays the blood supply estimate inside or near the indicated portion of the first model,
the blood supply estimate is an estimate of a blood supply in the vasculature, and
the method comprises, prior to the displaying, determining the estimate of blood supply in the vasculature based on the patient-specific vascular model.

19. The computer-readable medium of claim 16, wherein
the displaying displays the blood supply estimate inside or near the associated portion of the second model,
the blood supply estimate is an estimate of a blood supply in the tissue, and
the method comprises, prior to the displaying, determining the estimate of blood supply in the tissue based on the patient-specific tissue model.

20. The computer-readable medium of claim 15, wherein
the first model is the patient-specific tissue model,
the indicated portion of the first model represents a portion of the tissue,
the second model is the patient-specific vascular model, and the blood supply relationship is a relationship in which the associated portion of the second model represents a location of the vasculature that supplies blood to the portion of the tissue.

\* \* \* \* \*